United States Patent
Park

(10) Patent No.: US 10,640,821 B2
(45) Date of Patent: May 5, 2020

(54) METHOD AND KIT FOR DETECTING TARGET NUCLEIC ACID

(71) Applicants: PAXGENBIO CO., LTD., Gyeonggi-do (KR); Young Suk Park, Gyeonggi-do (KR)

(72) Inventor: Young Suk Park, Gyeonggi-do (KR)

(73) Assignees: PAXGENBIO CO., LTD., Gyeonggi-Do (KR); Park Young Suk, Gyeonggi-Do (KR)

( * ) Notice: Subject to any disclaimer, the term of this patent is extended or adjusted under 35 U.S.C. 154(b) by 163 days.

(21) Appl. No.: 15/572,479

(22) PCT Filed: May 17, 2016

(86) PCT No.: PCT/KR2016/005194
§ 371 (c)(1),
(2) Date: Nov. 7, 2017

(87) PCT Pub. No.: WO2016/190585
PCT Pub. Date: Dec. 1, 2016

(65) Prior Publication Data
US 2018/0148779 A1 May 31, 2018

(30) Foreign Application Priority Data
May 22, 2015 (KR) ........................ 10-2015-0071945

(51) Int. Cl.
*C12Q 1/6853* (2018.01)
*C12Q 1/6869* (2018.01)
(Continued)

(52) U.S. Cl.
CPC ............. *C12Q 1/6869* (2013.01); *C12Q 1/68* (2013.01); *C12Q 1/682* (2013.01); *C12Q 1/6806* (2013.01);
(Continued)

(58) Field of Classification Search
CPC .. C12Q 1/6834; C12Q 1/6837; C12Q 1/6844; C12Q 1/6846; C12Q 1/6853; C12Q 2565/625; C12Q 2565/629
See application file for complete search history.

(56) References Cited

U.S. PATENT DOCUMENTS

2004/0110167 A1 6/2004 Gerdes et al.
2011/0111389 A1 5/2011 Tam et al.
(Continued)

FOREIGN PATENT DOCUMENTS

| KR | 10-2003-0003181 A | 1/2003 | |
|---|---|---|---|
| KR | 10-2006-0015668 A | 2/2006 | |
| WO | WO-9947706 A1 * | 9/1999 | ........... C12Q 1/6874 |

OTHER PUBLICATIONS

Google translation of KR20060015668A (original document in Korean language is cited in IDS), 33 pages, Feb. 17, 2006.*
(Continued)

*Primary Examiner* — Diana B Johannsen
(74) *Attorney, Agent, or Firm* — Hultquist, PLLC; Steven J. Hultquist

(57) ABSTRACT

The present disclosure relates to a method and a kit for analyzing a nucleic acid amplification product, and more particularly to a method and kit of analyzing a nucleic acid amplification product using a labeled primer comprising (i) a binding region complementary to the target nucleic acid, (ii) a nucleic acid oligomer containing nucleotides non-complementary to the target nucleic acid, and (iii) a label, and using a membrane having immobilized thereon a probe that binds complementarily to the nucleic acid oligomer.

9 Claims, 3 Drawing Sheets
(2 of 3 Drawing Sheet(s) Filed in Color)
Specification includes a Sequence Listing.

Concept of Universal primer

Concept of Universal Lateral flow assay

(51) Int. Cl.
  *C12Q 1/68*        (2018.01)
  *C12Q 1/6837*      (2018.01)
  *C12Q 1/6825*      (2018.01)
  *C12Q 1/6806*      (2018.01)
  *C12Q 1/6811*      (2018.01)
  *C12Q 1/682*       (2018.01)
  *C12Q 1/6832*      (2018.01)
  *C12Q 1/6834*      (2018.01)
  *C12Q 1/6844*      (2018.01)
  *C12Q 1/6883*      (2018.01)
  *G01N 33/53*       (2006.01)
  *G01N 33/538*      (2006.01)

(52) U.S. Cl.
  CPC .......... *C12Q 1/6811* (2013.01); *C12Q 1/6825* (2013.01); *C12Q 1/6832* (2013.01); *C12Q 1/6834* (2013.01); *C12Q 1/6837* (2013.01); *C12Q 1/6846* (2013.01); *C12Q 1/6853* (2013.01); *C12Q 1/6883* (2013.01); *G01N 33/538* (2013.01); *G01N 33/5308* (2013.01)

(56) References Cited

U.S. PATENT DOCUMENTS

2012/0244529 A1   9/2012   Fuchs et al.
2014/0170649 A1   6/2014   Krebs et al.

OTHER PUBLICATIONS

Aveyard, J., et al., "One step visual detection of PCR products with gold nanoparticles and a nucleic acid lateral flow (NALF) device", "Chemical Communications", 2007, pp. 4251-4253, vol. 41.

Helb, D., et al., "Rapid Detection of *Mycobacterium tuberculosis* and Rifampin Resistance by Use of On-Demand, Near-Patient Technology", "Journal of Clinical Microbiology", Jan. 2010, pp. 229-237, vol. 48, No. 1.

Higuchi, R., et al., "Kinetic PCR Analysis: Real-time Monitoring of DNA Amplification Reactions", "Nature Bio/Technology", Sep. 1993, pp. 1026-1030, vol. 11.

Saiki, R. K., et al., "Primer-Directed Enzymatic Amplification of DNA with a Thermostable DNA Polymerase", "Science", Jan. 29, 1988, pp. 487-491, vol. 239.

Note: For the non-patent literature citations that no month of publication is indicated, the year of publication is more than 1 year prior to the effective filing date of the present application.

Hayashi, M., et al., "A New Protocol to Detect Multiple Foodborne Pathogens with PCR Dipstick DNA Chromatography after a Six-Hour Enrichment Culture in a Broad-Range Food Pathogen Enrichment Broth", "BioMed Research International", Dec. 3, 2013, pp. 1-10 (XP055520779), vol. 2013, Publisher: Hindawi Publishing Corporation.

Monden, Y., et al., "A rapid and enhanced DNA detection method for crop cultivar discrimination", "Journal of Biotechnology", Jun. 19, 2014, pp. 57-62 (XP029044530), vol. 185, Publisher: Elsevier.

Tasoglu, S., et al., "Advances in Nanotechnology and Microfluidics for Human Papillomavirus Diagnostics", "Proceedings of the IEEE", Feb. 2015, pp. 161-178 (XP011665085), vol. 103, No. 2, Publisher: IEEE.

Tian, L., et al., "Rapid and Sensitive PCR-Dipstick DNA Chromatography for Multiplex Analysis of the Oral Microbiota", "BioMed Research International", Jan. 1, 2014, pp. 1-10 (XP055380468), vol. 2014, Publisher: Hindawi Publishing Corporation.

* cited by examiner

SEQUENCE LISTING

<160> NUMBER OF SEQ ID NOS: 13

<210> SEQ ID NO 1
<211> LENGTH: 25
<212> TYPE: DNA
<213> ORGANISM: Artificial Sequence
<220> FEATURE:
<223> OTHER INFORMATION: probe binding region of primer

<400> SEQUENCE: 1

```
cgaggacgac gaggactccc accag                                              25

<210> SEQ ID NO 2
<211> LENGTH: 25
<212> TYPE: DNA
<213> ORGANISM: Artificial Sequence
<220> FEATURE:
<223> OTHER INFORMATION: probe binding region of primer

<400> SEQUENCE: 2
cgaggtaggc acgcagctcc accag                                              25

<210> SEQ ID NO 3
<211> LENGTH: 25
<212> TYPE: DNA
<213> ORGANISM: Artificial Sequence
<220> FEATURE:
<223> OTHER INFORMATION: probe binding region of primer

<400> SEQUENCE: 3
cgaggtaccc tggctgctgc accag                                              25

<210> SEQ ID NO 4
<211> LENGTH: 21
<212> TYPE: DNA
<213> ORGANISM: Artificial Sequence
<220> FEATURE:
<223> OTHER INFORMATION: Target complementary binding region

<400> SEQUENCE: 4
tcgatgtatg tcttgttgca g                                                  21

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
aggttacaat attgtaatgg gc                                                 22

<210> SEQ ID NO 6
<211> LENGTH: 20
<212> TYPE: DNA
<213> ORGANISM: Artificial Sequence
<220> FEATURE:
<223> OTHER INFORMATION: Target complementary binding region

<400> SEQUENCE: 6
aacatagctg ggcactatag                                                    20

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
catacacaac attgtgtgac g                                                  21

<210> SEQ ID NO 8
<211> LENGTH: 20
<212> TYPE: DNA
<213> ORGANISM: Artificial Sequence
```

-continued

```
<220> FEATURE:
<223> OTHER INFORMATION: Target complementary binding region

<400> SEQUENCE: 8
gaagagccaa ggacaggtac                                              20

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
tggtctcctt aaacctgtct tg                                           22

<210> SEQ ID NO 10
<211> LENGTH: 25
<212> TYPE: DNA
<213> ORGANISM: Artificial Sequence
<220> FEATURE:
<223> OTHER INFORMATION: primer binding region of probe

<400> SEQUENCE: 10
cgaggacgac gaggactccc accag                                        25

<210> SEQ ID NO 11
<211> LENGTH: 25
<212> TYPE: DNA
<213> ORGANISM: Artificial Sequence
<220> FEATURE:
<223> OTHER INFORMATION: primer binding region of probe

<400> SEQUENCE: 11
cgaggtaggc acgcagctcc accag                                        25

<210> SEQ ID NO 12
<211> LENGTH: 25
<212> TYPE: DNA
<213> ORGANISM: Artificial Sequence
<220> FEATURE:
<223> OTHER INFORMATION: primer binding region of probe

<400> SEQUENCE: 12
cgaggtaccc tggctgctgc accag                                        25

<210> SEQ ID NO 13
<211> LENGTH: 15
<212> TYPE: DNA
<213> ORGANISM: Artificial Sequence
<220> FEATURE:
<223> OTHER INFORMATION: oligomer of probe for immobilizing on membrane

<400> SEQUENCE: 13
tttttttttt ttttt                                                   15
```

METHOD AND KIT FOR DETECTING TARGET NUCLEIC ACID

CROSS-REFERENCE TO RELATED APPLICATIONS

This application is a U.S. national phase under the provisions of 35 U.S.C. § 371 of International Patent Application No. PCT/KR2016/005194 filed May 17, 2016, which in turn claims priority of Korean Patent Application No. 10-2015-0071945 filed May 22, 2015. The disclosures of such international patent application and Korean priority patent application are hereby incorporated herein by reference in their respective entireties, for all purposes.

TECHNICAL FIELD

The present disclosure relates to a method and a kit for analyzing a target nucleic acid, and more particularly to a method and a kit for detecting and analyzing a nucleic acid using a primer comprising (i) a binding region complementary to the target nucleic acid and (ii) a nucleic acid oligomer comprising nucleotides non-complementary to the target nucleic acid, and (iii) a primer with a label, and using a membrane having immobilized thereon a probe that binds complementarily to the nucleic acid oligomer.

BACKGROUND ART

Molecular diagnosis is used to detect the basic causes of disease, such as DNA or RNA molecules, in various diagnostic fields, including infectious disease diagnosis, cancer diagnosis, genetic disease diagnosis and personalized diagnosis fields. Typical molecular diagnosis techniques are PCR techniques for amplifying DNA within a short time (Saiki, R., et. al. Primer-directed enzymatic amplification of DNA with a thermostable DNA polymerase. Science 239, 487-91. 1998). However, in general PCR techniques, electrophoresis should be used to confirm amplified DNA. Before such electrophoresis, complicated procedures should be performed, including making agarose gel and staining DNA with EtBr or the like. For this reason, electrophoresis is not suitable for use in clinical laboratories.

Real-time PCR techniques that have recently been used are based on fluorescence, and thus electrophoresis is not required, but have a defect in that expensive instruments and expensive fluorescent reagents are used (Higuchi, R., et. al., Kinetic PCR Analysis: Real-time Monitoring of DNA Amplification Reactions. Nature Biotechnology 11, 1026-1030, 1993). In addition, these techniques have a shortcoming in that, because fluorescence wavelengths to be used are limited, it is difficult to practically perform multiplex PCR for five or more samples. For these reasons, there are many difficulties in performing inexpensive clinical tests by use of PCR techniques in laboratories, and thus PCR techniques are used mainly in large-sized hospitals such as university hospitals.

In recent years, GeneXpert system and reagents (Cepheid) for use in on-site diagnosis have been developed and marketed. However, the system and reagents are highly expensive, and thus are hardly used in general clinical tests (Helb, D., et. al., Rapid Detection of *Mycobacterium tuberculosis* and Rifampin Resistance by Use of On-Demand, Near-Patient Technology. J. Clin. Microbiol. 48, 229-237, 2010).

Other techniques include a nucleic acid lateral flow assay that is performed using a membrane instead of gel electrophoresis after PCR (Nucleic Acid Lateral Flow Assay) 가 있다 (Aveyard, J., et. al., One step visual detection of PCR products with gold nanoparticles and a nucleic acid lateral flow (NALF) device. Chem. Commun., 41, 4251-4253, 2007). However, this nucleic acid lateral flow assay is more complicated than gel electrophoresis techniques, and thus is impossible to use in laboratories. In addition, as there are technical limitations in a view that the sequence of a probe attached to the membrane should be used so that it can bind specifically to a PCR amplification product, the universal use of the nucleic acid lateral flow assay is limited.

Under this technical background, the present inventors have found that, when a nucleic acid oligomer in an artificially synthesized PCR primer is allowed to react with a probe complementary to the nucleic acid oligomer on a membrane regardless of types on amplification product, various PCR products can be universally identified using a single type of membrane, thereby completing the present disclosure.

The information disclosed in the Background Art section is only for the enhancement of understanding of the background of the present disclosure, and therefore may not contain information that forms a prior art that would already be known to a person of ordinary skill in the art.

DISCLOSURE OF INVENTION

Technical Problem

The present inventors have recognized the above-mentioned problems occurring in the prior art, and it is an object of the present disclosure to provide a universal method for detecting and analyzing a plurality of target nucleic acids, which can analyze amplified nucleic acids resulting from amplification of the target nucleic acids in a more accurate and simpler manner than conventional electrophoresis methods, and which can simultaneously identify the plurality of target nucleic acids, and a kit for use in the method.

Technical Solution

To achieve the above object, the present disclosure provides a method for detecting a target nucleic acid, comprising the steps of:

(a) amplifying the target nucleic acid by reacting a sample comprising the target nucleic acid with a primer comprising (i) a binding region complementary to the target nucleic acid and (ii) a nucleic acid oligomer comprising nucleotides non-complementary to the target nucleic acid, and (iii) a primer with a label;

(b) reacting a product amplified in step (a) with a membrane having immobilized thereon a probe that binds complementarily to the nucleic acid oligomer; and (c) confirming whether or not a reaction is shown from the label to detect whether or not the target nucleic acid would be amplified.

The present disclosure also provides a kit for detecting a target nucleic acid, comprising: (a) a primer comprising (i) a binding region complementary to the target nucleic acid and (ii) a nucleic acid oligomer comprising nucleotides non-complementary to the target nucleic acid, and (iii) a primer with a label; and (b) a membrane having immobilized thereon a probe that binds complementarily to the nucleic acid oligomer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
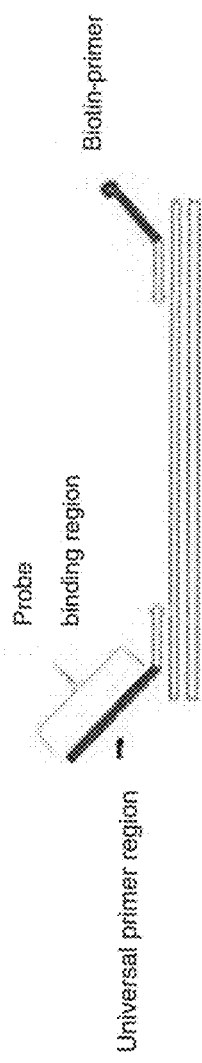
FIG. 1 shows a method for detecting a nucleic acid amplification product according to an embodiment of the present disclosure.
Figure 1:
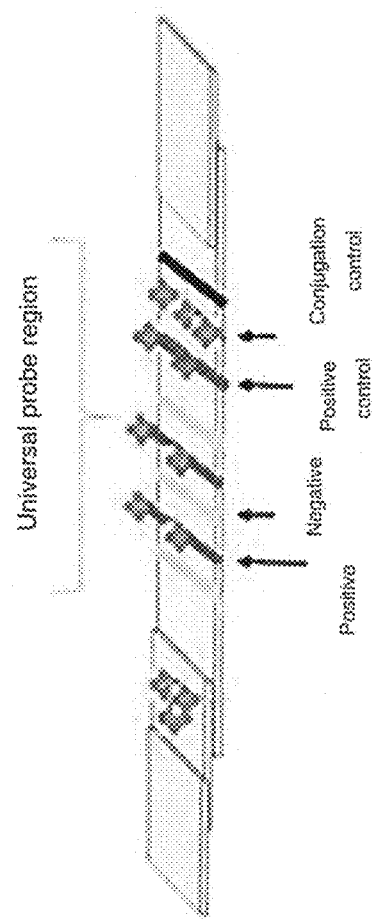

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In one aspect, the present disclosure is directed to a method for detecting a target nucleic acid, comprising the steps of:

(a) amplifying the target nucleic acid by reacting a sample comprising the target nucleic acid with a primer comprising (i) a binding region complementary to the target nucleic acid and (ii) a nucleic acid oligomer comprising nucleotides non-complementary to the target nucleic acid, and (iii) a primer with a label;

(b) reacting a product amplified in step (a) with a membrane having immobilized thereon a probe that binds complementarily to the nucleic acid oligomer; and (c) confirming whether or not a reaction is shown from the label to detect whether or not the target nucleic acid would be amplified.

A method that is most frequently used in molecular diagnosis is based on polymerase chain reaction (PCR). This method is a technique for amplifying a trace amount of specific DNA within several hours, and the sensitivity thereof can be dramatically increased compared to that of immunodiagnosis. However, general PCR techniques are inconvenient in that amplification products should be confirmed by electrophoresis on gel. In recent years, real-time PCR techniques based on fluorescence have been used, but these techniques require a complex and expensive system and expensive PCR reagents, and thus are hardly used in general laboratories.

Accordingly, the present disclosure provides a technology in which amplified genes resulting from amplification of the target nucleic acids, including PCR, is analyzed in a more accurate and simpler manner than conventional electrophoresis methods.

The method for detecting a target nucleic acid according to the present disclosure comprises (a) synthesizing a primer comprising (i) a binding region complementary to the target nucleic acid and (ii) a nucleic acid oligomer comprising nucleotides non-complementary to the target nucleic acid, and (iii) a primer with a label, and reacting the target nucleic acid with the synthesized labeled primer, thereby amplifying the target nucleic acid.

To amplify target gene (nucleic acid) by PCR, an about 10-40 bp, preferably about 20-30 bp nucleic acid oligomer comprising nucleotides non-complementary to the target nucleic acid, which is a gene having no connection with the target nucleic acid, is added to a primer, and the target gene is amplified using the synthesized primer. Then, an about 10-40 bp, preferably abut 20-30 bp of probe complementary to the nucleic acid oligomer is immobilized on a membrane, and the probe is hybridized to the target nucleic acid.

An about 10-40 bp, preferably 20-30 bp, nucleic acid oligomer is added to the end of a primer that is used in a general multiplex-PCR assay, and an amplification product obtained using the primer is reacted with a complementary probe oligomer on a membrane, whereby whether or not the target nucleic acid would be amplified can be determined.

This makes it possible to simultaneously diagnose several kinds of diseases. That is, when multiplex PCR is performed using primers having several to several ten different oligomer sequences, and then the PCR amplification products are allowed to react with probes complementary to the oligomer sequences, several to several ten amplification products can be identified using a single lateral flow membrane.

Thus, as a lateral flow membrane can be used commonly in various multiplex PCR assays, large amounts of results from a lateral flow membrane can be produced. This indicates that various amplification products can be identified using a single lateral flow membrane. That is, as amplification products can be confirmed using the same membrane regardless of the kind of PCR amplification product, production cost reduction and quality control can be easily achieved, thereby increasing product productivity.

An embodiment of a method of analyzing nucleic acid amplification products so as to enable HPV 16 and 18 to be simultaneously diagnosed is described in Example 1 below. In this case, the nucleic acid oligomer may comprise one or more sequences selected from the group consisting of SEQ ID NOs: 1 to 3.

The method for detecting a target nucleic acid according to the present disclosure comprises a step of (b) reacting a product amplified in step (a) with a membrane having immobilized thereon a probe that binds complementarily to the nucleic acid oligomer.

In step (b), the amplification product of step (a) may be injected into the lateral side of the membrane so that the nucleic acid oligomer in the amplification product can complementarily hybridize to the probe immobilized on the membrane, while the amplification product moves.

An embodiment of a method of analyzing nucleic acid amplification products so as to enable HPV 16 and 18 to be simultaneously diagnosed is described in Example 1 below. In this case, the probe that binds complementarily to the nucleic acid oligomer may comprise one or more sequences selected from the group consisting of SEQ ID NOs: 10 to 12.

In an alternative embodiment, the probe of step (b) may additionally comprises a nucleic acid oligomer for immobilization on the membrane, and the probe may further comprises a 10-40 bp oligomer having repeated nucleotide sequences.

An embodiment of a method of analyzing nucleic acid amplification products so as to enable HPV 16 and 18 to be simultaneously diagnosed is described in Example 1 below. In this case, the additional nucleic acid oligomer may comprise a sequence of SEQ ID NO: 13.

The method for detecting a target nucleic acid according to the present disclosure comprises a step of (c) confirming whether or not the label would be chromogenic, thereby detecting whether or not the target nucleic acid would be amplified.

In one embodiment, the label may be biotin, Cy5, Cy3, FITC, EDANS (5-(2'-aminoethyl)amino-1-naphthalenesulfonic acid), tetramethylrhodamine (TMR), tetramethylrhodamine isocyanate (TMRITC), x-rhodamine, DIG, or an antibody, but is not limited thereto.

In addition, a reaction with a binding agent that elicits a chromogenic signal of the label may be added in step (c) to confirm a chromogenic or fluorescent signal and detect amplification of the target nucleic acid. In this case, the binding agent may be streptavidin, but is not limited thereto.

When amplification is performed using a primer having biotin attached thereto, the biotin can bind to streptavidin on the membrane. According to the tendency of beads attached to streptavidin, target nucleic acid amplification can be confirmed by a chromogenic signal in the case of gold particles, or can be confirmed by fluorescent signals having various wavelengths. Depending on the kind of probe attached to the membrane, several to several ten target nucleic acids can be detected.

In another aspect, the present disclosure is directed to a kit for detecting a target nucleic acid, comprising: (a) a primer comprising (i) a binding region complementary to the target nucleic acid and (ii) a nucleic acid oligomer comprising nucleotides non-complementary to the target nucleic acid, and (iii) a primer with a label; and (b) a membrane having immobilized thereon a probe that binds complementarily to the nucleic acid oligomer.

The kit can be various configured depending on use purpose, and it can be used for detection or identification of the amplified target nucleic acid. The kit of the present disclosure may optionally comprise, depending on the use purpose, reagents required for performing a nucleic acid amplification PCR reaction, such as polymerase, buffer, and deoxyribonucleotide-5-triphosphate. In some embodiments, the kit of the present disclosure may also further include various polynucleotide molecules, and various buffers and reagents.

The optimal amount of a reagent, a buffer or a reactant used for a specific reaction in the kit can be determined by those skilled in the art, and the kit may be manufactured as a separate package or compartment containing the primer of step (a) and the membrane having immobilized thereon the probe of step (b) as mentioned above.

Examples

Hereinafter, the present disclosure will be described in further detail with reference to examples. It will be obvious to a person having ordinary skill in the art that these examples are for illustrative purposes only and are not to be construed to limit the scope of the present disclosure.

1. Design for Simultaneous Diagnosis of HPV 16 and 18

HPV (human papillomavirus) is a virus causing cervical cancer, and about 100 HPV types have been reported. Among these HPV types, HPV 16 and HPV 18 are known to belong to a high-risk group and to be deeply associated with cervical cancer (Walboomers, J., et. al., Human papillomavirus is a necessary cause of invasive cervical cancer worldwide. The Journal of Pathology 189, 12-19, 1999).

To diagnose HPV 16 and HPV 18 simultaneously, genes specific for HPV 16 and HPV 18 are used, and beta-globin gene present in all human cells is used as a control, and the three genes are simultaneously amplified.

Primer sequences used for PCR are shown in Table 1 below. Each primer is composed of a region for amplifying each gene and a region to which a probe can bind.

TABLE 1

| Primer | | Sequence |
|---|---|---|
| HPV 16 | Forward | CGAGGACGACGAGGACTCCCACCAG (probe binding region: SEQ ID NO: 1)-TCGATGTATGTCTTGTTGCAG(HPV 16 region: SEQ ID NO: 4) |
| | Reverse | AGGTTACAATATTGTAATGGGC-Biotin (SEQ ID NO: 5) |
| HPV 18 | Forward | CGAGGTAGGCACGCAGCTCCACCAG(probe binding region: SEQ ID NO: 2)-AACATAGCTGGGCACTATAG (HPV 18 region: SEQ ID NO: 6) |
| | Reverse | CATACACAACATTGTGTGACG-Biotin (SEQ ID NO: 7) |
| β-globin | Forward | CGAGGTACCCTGGCTGCTGCACCAG (probe binding region: SEQ ID NO: 3)-GAAGAGCCAAGGACAGGTAC (β-globin region: SEQ ID NO: 8) |
| | Reverse | TGGTCTCCTTAAACCTGTCTTG-Biotin (SEQ ID NO: 9) |

Figure 2:
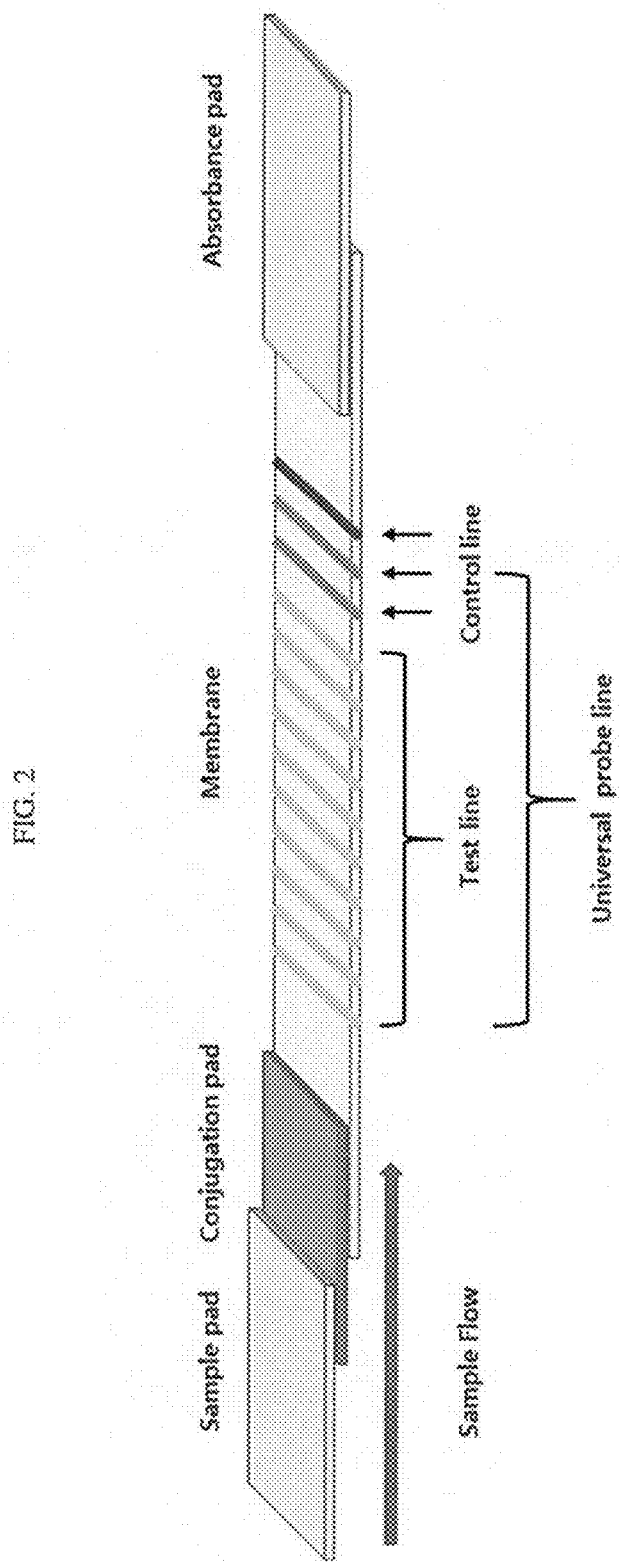
FIG. 2 shows a universal technique of detecting and analyzing a target nucleic acid by a lateral flow assay according to an embodiment of the present disclosure.

In addition, probe sequences attached to a lateral flow membrane and to react with PCR amplification products are shown in FIG. 2 below. To facilitate the binding of each primer-binding region to the membrane, each probe sequence comprises 10-30 oligo-thymines.

TABLE 2

| Primer | Sequence |
|---|---|
| HPV 16 | CGAGGACGACGAGGACTCCCACCAG (primer binding region: SEQ ID NO: 10)-TTTTTTTTTTTTTT (10-30 mer: SEQ ID NO: 13) |
| HPV 18 | CGAGGTAGGCACGCAGCTCCACCAG (primer binding region: SEQ ID NO: 11)-TTTTTTTTTTTTTT (10-30 mer: SEQ ID NO: 13) |
| β-globin | CGAGGTACCCTGGCTGCTGCACCAG (primer binding region: SEQ ID NO: 12)-TTTTTTTTTTTTTT (10-30 mer: SEQ ID NO: 13) |

Figure 3:
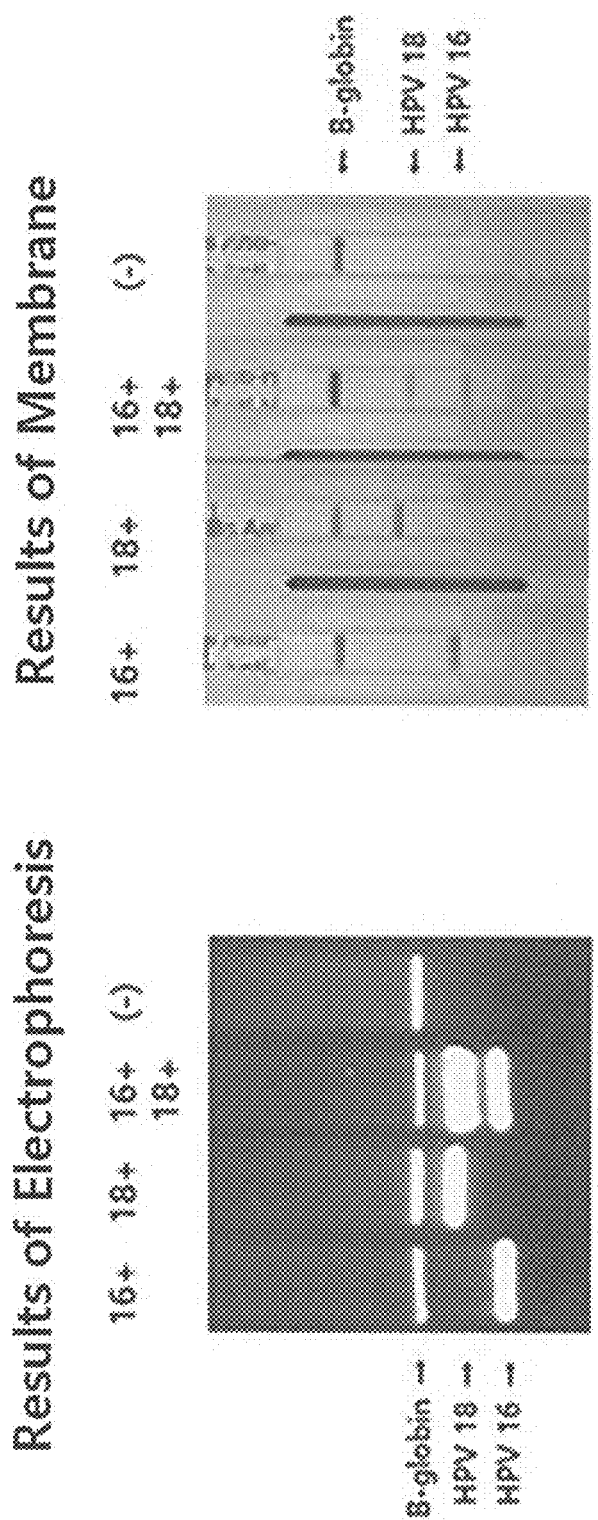
FIG. 3 shows the results of analyzing the products of amplification of HPV 16 and HPV 18 target nucleic acids by a method for detection of target nucleic acid amplification products according to an embodiment of the present disclosure.

2. Comparison Between Electrophoresis Results and Lateral Flow Membrane Assay Results Multiplex PCR was performed, and then 10 μl of the PCR product was electrophoresed on 1.5% agarose gel for 30 minutes, and the results were analyzed. Meanwhile, 10 μl of the PCR product was reacted on a lateral flow membrane for 15 minutes, and the results were analyzed. FIG. 3 shows the comparison between the electrophoresis results and the lateral flow membrane assay results. As can be seen in FIG. 3, the two assay methods showed the same results.

INDUSTRIAL APPLICABILITY

As described above, in the method for detecting target nucleic acid and the kit for detecting target nucleic acid according to the present disclosure, a probe complementary to an artificially synthesized primer is immobilized on a membrane so that the product of amplification of the target nucleic acid can be detected regardless of the sequence thereof, indicating that various amplification products can be identified using a single membrane. The method and kit according to the present disclosure can be universally used for various amplification products, unlike a conventional art in which a one-to-one reaction between a primer and a probe. Thus, a universal membrane can be used instead of a membrane that should be separately used for each target nucleic acid. This indicates that the universal membrane can be produced with increased productivity.

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

The invention claimed is:

1. A method for detecting a target nucleic acid, comprising the steps of:

(a) amplifying the target nucleic acid by reacting a sample comprising the target nucleic acid with a labeled primer comprising (i) a binding region complementary to the target nucleic acid and (ii) a nucleic acid oligomer comprising nucleotides non-complementary to the target nucleic acid, and (iii) a label;

(b) reacting a product amplified in step (a) with a membrane having immobilized thereon a probe that binds complementarily to the nucleic acid oligomer; and (c) detecting whether the label has been reacted in step (b), wherein the reacted label is indicative of amplification of the target nucleic acid, and wherein the nucleic acid oligomer comprises one or more nucleotide sequences selected from the group consisting of SEQ ID NOS: 1-3.

2. The method of claim 1, wherein the nucleic acid oligomer of step (a) is 25-40 bp in length.

3. The method of claim 1, wherein the step (b) comprises injecting the amplification product of step (a) into a lateral side of the membrane so that the nucleic acid oligomer comprised in the amplification product can complementarily hybridize to the probe immobilized on the membrane, while the amplification product moves.

4. The method of claim 1, wherein the probe that binds complementarily to the nucleic acid oligomer of step (b) comprises one or more sequences selected from the group consisting of SEQ ID NOs: 10 to 12.

5. The method of claim 1, wherein the probe of step (b) additionally comprises a nucleic acid oligomer for immobilization on the membrane.

6. The method of claim 5, wherein the additional nucleic acid oligomer comprises a sequence of SEQ ID NO: 13.

7. The method of claim 1, wherein the label is biotin, Cy5, Cy3, FITC, EDANS (5-(2'-aminoethyl)amino-1-naphthalenesulfonic acid), tetramethylrhodamine (TMR), tetramethylrhodamine isocyanate (TMRITC), x-rhodamine, DIG, or an antibody.

8. The method of claim 1, wherein step (c) further comprises a reaction with a binding agent that elicits a chromogenic signal of the label.

9. The method of claim 8, wherein the binding agent is streptavidin.

* * * * *